(12) United States Patent
Maxfield (10) Patent No.: US 10,363,373 B2
(45) Date of Patent: Jul. 30, 2019

(54) MEDICAMENT DELIVERY DEVICE

(71) Applicant: CAREBAY EUROPE LTD, Sliema (MT)

(72) Inventor: Brian Maxfield, Delray Beach, FL (US)

(73) Assignee: SHL MEDICAL AG, Zug (CH)

(*) Notice: Subject to any disclaimer, the term of this patent is extended or adjusted under 35 U.S.C. 154(b) by 0 days.

(21) Appl. No.: 15/557,976

(22) PCT Filed: Mar. 23, 2016

(86) PCT No.: PCT/EP2016/056369
§ 371 (c)(1),
(2) Date: Sep. 13, 2017

(87) PCT Pub. No.: WO2016/169718
PCT Pub. Date: Oct. 27, 2016

(65) Prior Publication Data
US 2018/0036491 A1    Feb. 8, 2018

(30) Foreign Application Priority Data
Apr. 24, 2015   (SE) ..................................... 1550495

(51) Int. Cl.
*A61M 5/315* (2006.01)
*A61M 5/20* (2006.01)
(Continued)

(52) U.S. Cl.
CPC ...... *A61M 5/31585* (2013.01); *A61M 5/2033* (2013.01); *A61M 5/3202* (2013.01);
(Continued)

(58) Field of Classification Search
CPC ............ A61M 5/31551; A61M 5/3155; A61M 5/31585; A61M 5/2033; A61M 5/3202;
(Continued)

(56) References Cited

U.S. PATENT DOCUMENTS 5,279,586 A * 1/1994 Balkwill ............. A61M 5/3158
222/309
5,300,030 A * 4/1994 Crossman ........... A61M 5/2033
604/134
(Continued)

FOREIGN PATENT DOCUMENTS

WO    2013/178512 A1    12/2013
WO    WO-2013178512 A1 * 12/2013   .......... A61M 5/2033
(Continued)

OTHER PUBLICATIONS

International Search Report and Written Opinion for Int. App. No. PCT/EP2016/056369, dated Jun. 28, 2016.

*Primary Examiner* — Nathan R Price
*Assistant Examiner* — Mark Alan Igel
(74) *Attorney, Agent, or Firm* — McDonnell Boehnen Hulbert & Berghoff LLP (57) ABSTRACT

A medicament delivery device is presented having an elongated housing extending in a longitudinal direction, which housing is arranged to accommodate a medicament container, an end cap arranged with a first attachment element designed to engage with a second attachment element on the housing for attaching the end cap to the housing, a rotator rotatably arranged inside the housing, an activator axially slidable with respect to the housing from an extended position to a retracted position and operably connected to the rotator such as to rotate the rotator from an initial non-activated rotational position and an activated rotational position when the activator is moved from the extended to the retracted position. The rotator further comprises a blocking element arranged to cooperate with the first attachment element for preventing disengagement of the first attachment element from the second attachment element when the rotator is in the activated rotational position.

18 Claims, 7 Drawing Sheets

(51) Int. Cl.
*A61M 5/32* (2006.01)
*A61M 5/24* (2006.01)
(52) U.S. Cl.
CPC ............... *A61M 2005/2013* (2013.01); *A61M 2005/2477* (2013.01); *A61M 2207/00* (2013.01)
(58) Field of Classification Search
CPC ...... A61M 5/31525; A61M 2005/2013; A61M 2005/2477
See application file for complete search history.

(56) References Cited

U.S. PATENT DOCUMENTS

| | | | | |
|---|---|---|---|---|
| 5,921,966 | A * | 7/1999 | Bendek | A61M 5/24 604/207 |
| 2010/0049125 | A1* | 2/2010 | James | A61M 5/2033 604/110 |
| 2010/0152659 | A1* | 6/2010 | Streit | A61M 5/2033 604/136 |

FOREIGN PATENT DOCUMENTS

| | | |
|---|---|---|
| WO | 2014/095424 A1 | 6/2014 |
| WO | 2015/001819 A1 | 1/2015 |

* cited by examiner

MEDICAMENT DELIVERY DEVICE

CROSS REFERENCE TO RELATED APPLICATIONS

The present application is a U.S. National Phase Application pursuant to 35 U.S.C. § 371 of International Application No. PCT/EP2016/056369 filed Mar. 23, 2016, which claims priority to Swedish Patent Application No. 1550495-4 filed Apr. 24, 2015. The entire disclosure contents of these applications are herewith incorporated by reference into the present application.

TECHNICAL AREA

The present disclosure relates to a medicament delivery device, and in particular a medicament delivery device provided with a drive mechanism arranged with a compression spring.

BACKGROUND

A medicament delivery device may comprise a number of components that are manufactured and assembled in order to provide the desired functions. The medicament delivery devices often comprise elongated housing parts that are arranged to house the assembled components. These may for example include power units or drive mechanisms that are capable of delivering forces when activated, which forces may be used for performing different functions such as e.g. penetration and injection if the medicament delivery device is an injection device.

In many cases the drive mechanisms are assembled with the power source, often a compression drive spring, in a tensioned state. The drive springs are often held in this tensioned state by components of the unit and do not in that non-active state exert any force on the housing of the medicament delivery device.

When the components are assembled inside the housing, it is often enclosed by some sort of enclosure cap, such as an end cap that is attached. The attachment may be performed in many ways such as gluing, plastic welding, screw threads or bayonet threads. These attachment means often provide a secure attachment, but are not optimal from an assembly point of view since they either take quite an amount of time to perform an attachment, or they make the moulding dies complicated in order to get the form and the required tolerances, which increases the manufacturing costs. This may not be acceptable if for example the medicament delivery device is a so called disposable that is thrown or discarded after us.

Therefore, flexible arms with snap-in attachments are often used, providing a fast assembly operation, with moderately complicated forms. However, since the flexibility is utilized when assembly is performed, there is a risk that the attachment is disengaged during use. This risk is especially pronounced if the attachment is exposed to a force, which may be the case when the medicament delivery device is activated and for example a drive spring is released. In order for the spring to exert a force on a medicament container for expelling a dose of medicament, the other end of the spring has to have a fixed support, which in many cases may constitute a surface of the end cap.

This may be a major drawback because the medicament delivery device may then break leading on the one hand to a non-delivery of medicament and on the other hand may injure the user.

SUMMARY

In the present application, when the term "distal part/end" is used, this refers to the part/end of the device, or the parts/ends of the members thereof, which during use of the device is located the furthest away from the medicament delivery site of the patient. Correspondingly, when the term "proximal part/end" is used, this refers to the part/end of the device, or the parts/ends of the members thereof, which during use of the device is located closest to the medicament delivery site of the patient.

The aim of the present disclosure is to remedy the drawbacks of the state of the art devices. This aim is obtained by a drive mechanism having the features of the independent patent claim. Preferable embodiments of the disclosure form the subject matter of the dependent patent claims.

The present disclosure relates to a medicament delivery device comprising an elongated housing extending in a longitudinal direction, where the housing is arranged to accommodate a medicament container. An end cap is further arranged with a first attachment element designed to engage with a second attachment element on the housing for attaching the end cap to the housing, thereby enclosing the medicament delivery device.

The medicament delivery device may be provided with a rotator movably arranged inside the housing as well as an activator axially slidable with respect to the housing from an extended position to a retracted position and operably connected to the rotator such as to rotate the rotator from an initial non-activated rotational position and an activated rotational position when the activator is moved from the extended to the retracted position.

The rotator may further comprise a blocking element arranged to cooperate with the first attachment element for preventing disengagement of the first attachment element from the second attachment element when the rotator is in the activated rotational position. In this manner it is ensured that the end cap cannot be removed from the housing when the medicament delivery device when activated.

According to one feasible solution, the first attachment elements may comprise proximally directed arms, flexible in a direction generally transverse to the longitudinal direction and outwardly directed protrusions arranged on the free ends of the arms. These cooperate with the second attachment elements that may comprise recesses arranged to accommodate the protrusions. This solution provides a facilitated attachment of the end cap in that the arms may flex when the end cap is assembled, but which arms are prevented from flexing by the blocking elements when the medicament delivery device is activated.

According to a further favorable solution, the rotator may be generally tubular and in that respect the blocking element may comprise radially outwardly directed wall portions of the rotator. As an alternative, the blocking element may comprise radially outwardly extending protrusions arranged adjacent the free ends of the arms. With such a solution, the protrusions may also extend in a generally circumferential direction of the rotator.

As stated above, the blocking element may preferably be arranged to prevent disengagement when the medicament delivery device is activated, but to allow attachment of the end cap with the housing and engagement of the attachment elements when the medicament delivery device is in an initial, non-activated state. Thereby the use of flexible attachment elements can be used without the risk of the attachment elements flexing during use of the medicament delivery device, which otherwise would be a major drawback, especially when tensioned drive springs are used for delivering doses of medicament.

When a rotator is used, the protrusions may be arranged adjacent to the free ends of the arms in rotational positions of the rotator except in the non-activated rotational position of the rotator. Further, the rotator may preferably be rotatably journalled in the end cap.

The medicament delivery device may further comprise a power unit comprising a plunger rod arranged to act on the medicament container for expelling a dose of medicament, wherein the power unit further comprising a drive spring operably connected to the plunger rod for driving the plunger rod for expelling a dose of medicament, and that the rotator comprises a plunger rod locking element for releasably locking the plunger rod with the drive spring in a tensioned state.

In that respect, the plunger rod locking element may be arranged to release the plunger rod when the activator has rotated the rotator to the activated rotational position.

These and other aspects of, and advantages with, the present disclosure will become apparent from the following detailed description of the disclosure and from the accompanying drawings.

BRIEF DESCRIPTION OF DRAWINGS

In the following detailed description of the disclosure, reference will be made to the accompanying drawings, of which

DETAILED DESCRIPTION

Figure 2A:
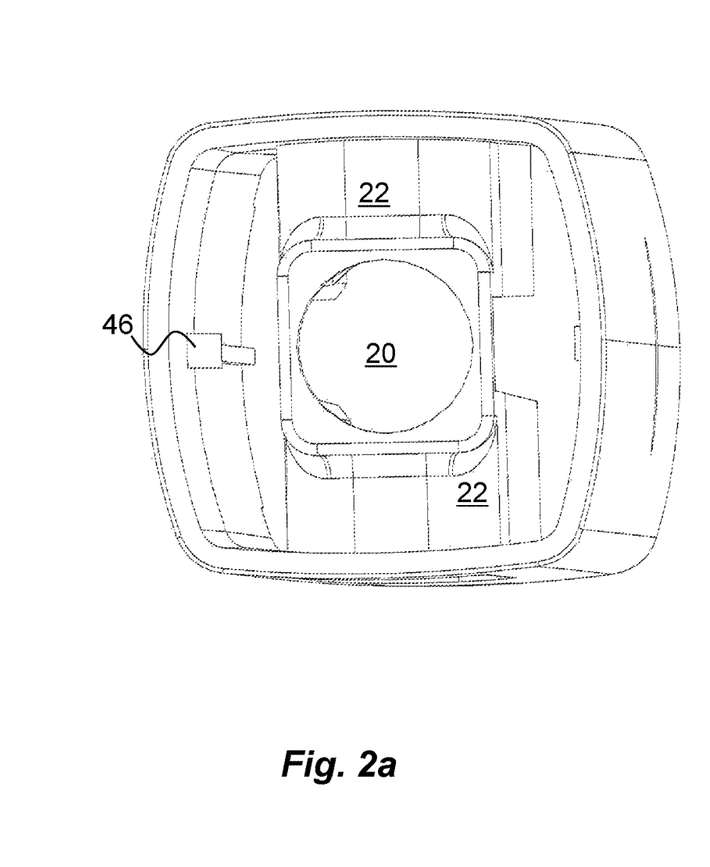
FIG. 2 is a detailed view of a housing comprised in the medicament delivery device of FIG. 1.
Figure 2B:
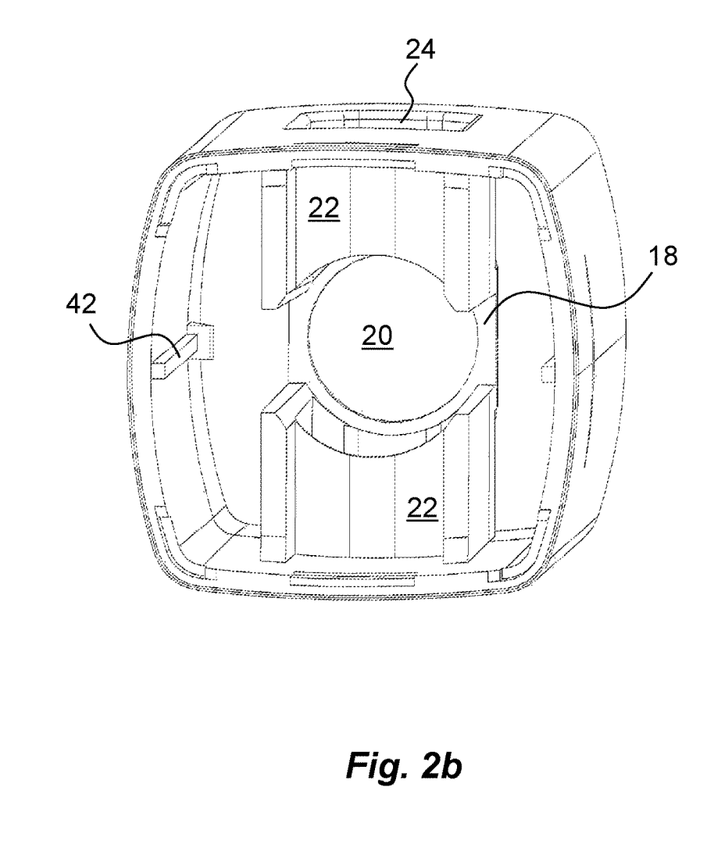

The embodiment shown of a medicament delivery device comprises a generally elongated housing 10 having a proximal end 12 and a distal end 14. The housing 10 is further arranged to accommodate a medicament container 16. Thereby a support surface 18, FIG. 2, is arranged with a central passage 20 through which a proximal end of the medicament container 16 may protrude and wherein a neck portion of the medicament container 16 may rest as seen in FIG. 3b, providing a stop surface in the proximal direction. The support surface 18 is an integral part of wall elements 22 surrounding openings or windows 24 in the housing. The wall elements 22 further act as supports for the medicament container 16 in the transversal directions. The medicament container 16 is arranged with a suitable medicament delivery member 26 that in the embodiment shown is an integrated injection needle. It is however to be understood that other types of medicament delivery members may be used such as attachable injection needles, wherein different types of attachment elements may be utilized such as screw threads, bayonet fittings, luer connections, etc. The medicament delivery member is preferably protected before use by a medicament delivery member shield 27, in the embodiment shown, a so-called rigid needle shield or RNS. It is however to be understood that other types of medicament delivery member shields may be used in order to obtain the desired protection of the medicament delivery member. The medicament container is further arranged with a movable stopper 28.

The proximal end 12 of the housing is arranged with a central passage 30. An activator in the form of a medicament delivery member guard 32 is arranged to fit into the central passage 30 and to be movable in the longitudinal direction. The medicament delivery member guard 32 is arranged with a proximal end wall 34 having a central passage 36. The medicament delivery member guard 32 is further arranged with two distally directed arms 38 that run along inner surfaces of the housing. Each arm 38 is arranged with a longitudinal groove 40, in which a guide ledge 42, FIG. 2a, arranged on the inner surface of the housing, may fit. Further, a longitudinal slit 44 is arranged on the arms 38, in which a stop ledge 46, FIG. 2b, may fit. At a distal end of the arms 38, inwardly directed protrusions 48 are arranged, the function of which will be explained. A medicament delivery member guard return spring 50 is further arranged between a proximally directed surface of the wall parts 22 and a distally directed surface of the end wall 34 of the medicament delivery member guard 32.

Figure 1:
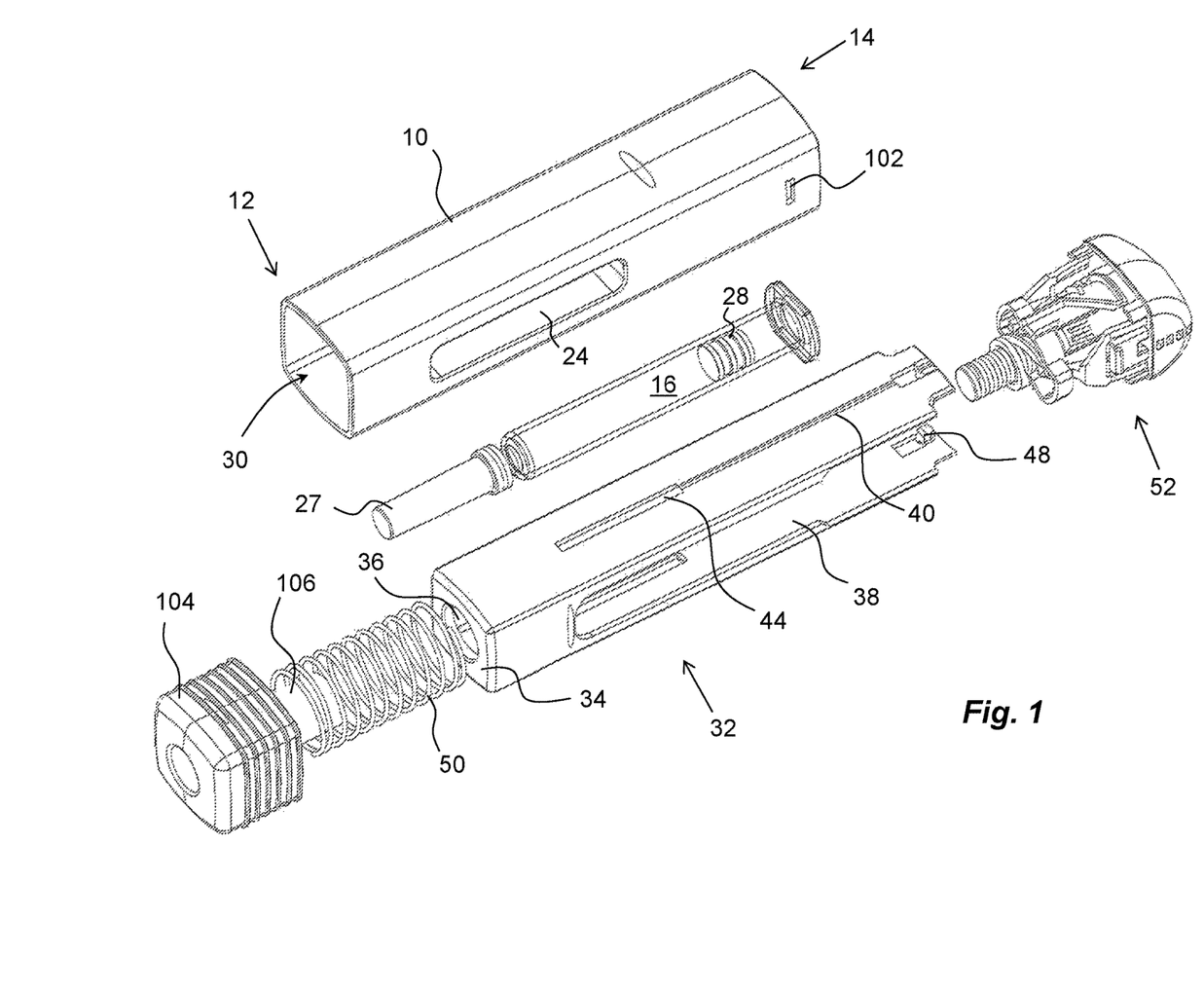
FIG. 1 is an exploded view of a medicament delivery device comprising a drive mechanism according to the present disclosure.
Figure 5:
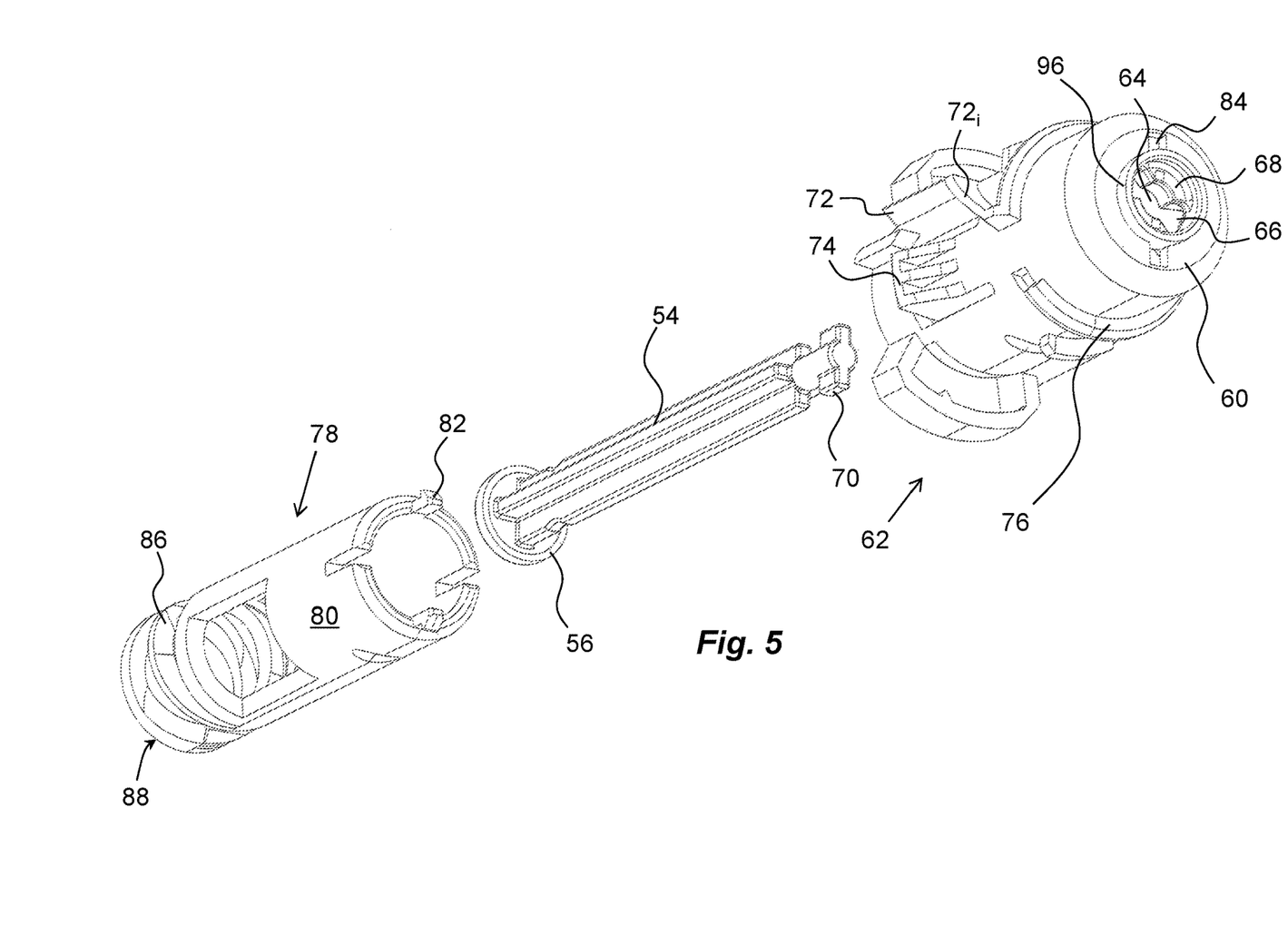

The medicament delivery device is further arranged with a power unit 52, FIGS. 1 and 5. It comprises a generally elongated plunger rod 54 provided with a disc 56 at its proximal end, which disc 56 has a diameter somewhat smaller than the inner diameter of the medicament container 16 and which disc 56 is to be in contact with the stopper 28 of the medicament container 16. The plunger rod 54 is surrounded by, and coaxial with, a compression drive spring 58 having its proximal end in contact with a distally directed surface of the disc 56 of the plunger rod 54, and with its distal end in contact with a proximally directed surface of an end wall 60 of a generally tubular rotator 62, FIG. 5.

The end wall 60 of the rotator 62 is arranged with a central passage 64 through which the plunger rod 54 may extend. The passage 64 is further arranged with cut-out sectors 66 with land sectors 68 in between, where the land sectors constitute plunger rod locking elements as will be described in detail below. The plunger rod 54 is in that respect arranged with radially extending wings 70 at its distal end, which wings 70 fit into the cut-out sectors 66 and can rest on the distally directed surfaces of the land sectors 68, as will be described.

The rotator 62 is further arranged with guide ridges 72 that are intended to cooperate with the protrusions 48 of the medicament delivery member guard 32 as will be described, wherein some sections $72_i$ of the guide ridges are inclined in relation to the longitudinal direction of the device. The rotator 62 is further arranged with wedge-shaped protrusions 74 arranged on generally radially flexible tongues, positioned adjacent the guide ridges 72, which wedge-shaped protrusions 74 are intended to lock the medicament delivery member guard 32 after completed use of the device as will be described. The rotator 62 is further arranged with blocking elements 76 that in the embodiment shown is designed as circumferentially extending ledges on the outer surface of the rotator 62, FIG. 5. The ledges 76 have a certain extension and position along the circumference, the function of which will be described below.

Figure 7:
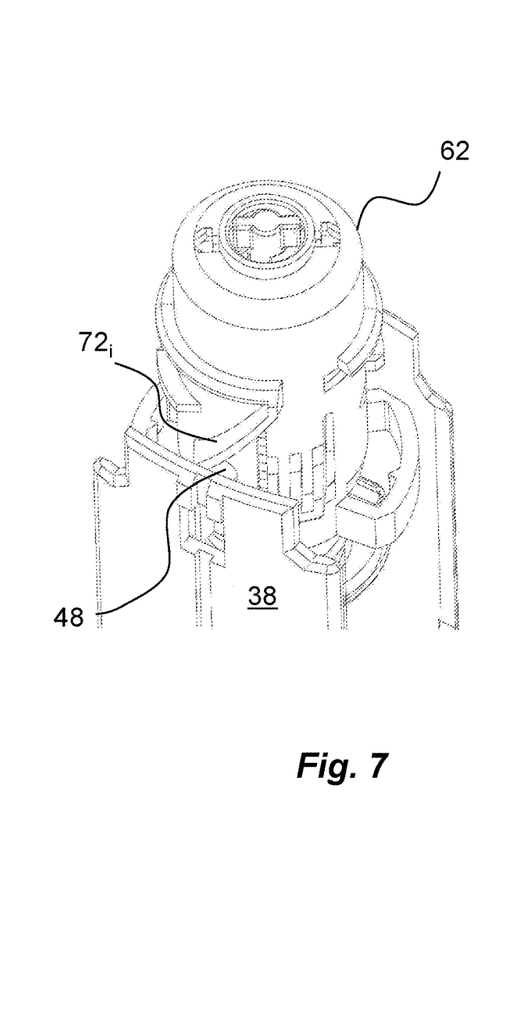

Positioned inside and coaxial with the rotator 62 is a spring guide 78, FIG. 5, having a generally tubular body part 80. A distal end surface of the body 80 is arranged with distally directed hooks 82, which are arranged to fit into passages 84 in the end wall 60 of the rotator 62, for attaching the spring guide 78 with the rotator 62. At the proximal end of the spring guide 78, a compression spring 86 is arranged, either attached to or made integral as seen in FIG. 7. The compression spring 86 is arranged with a ring-shaped end surface 88, which is intended to be in engagement with a distal end surface of the medicament container 16, urging the latter in the proximal direction against the seat 18 of the housing, as seen in FIG. 3.

Figures 4, 6:
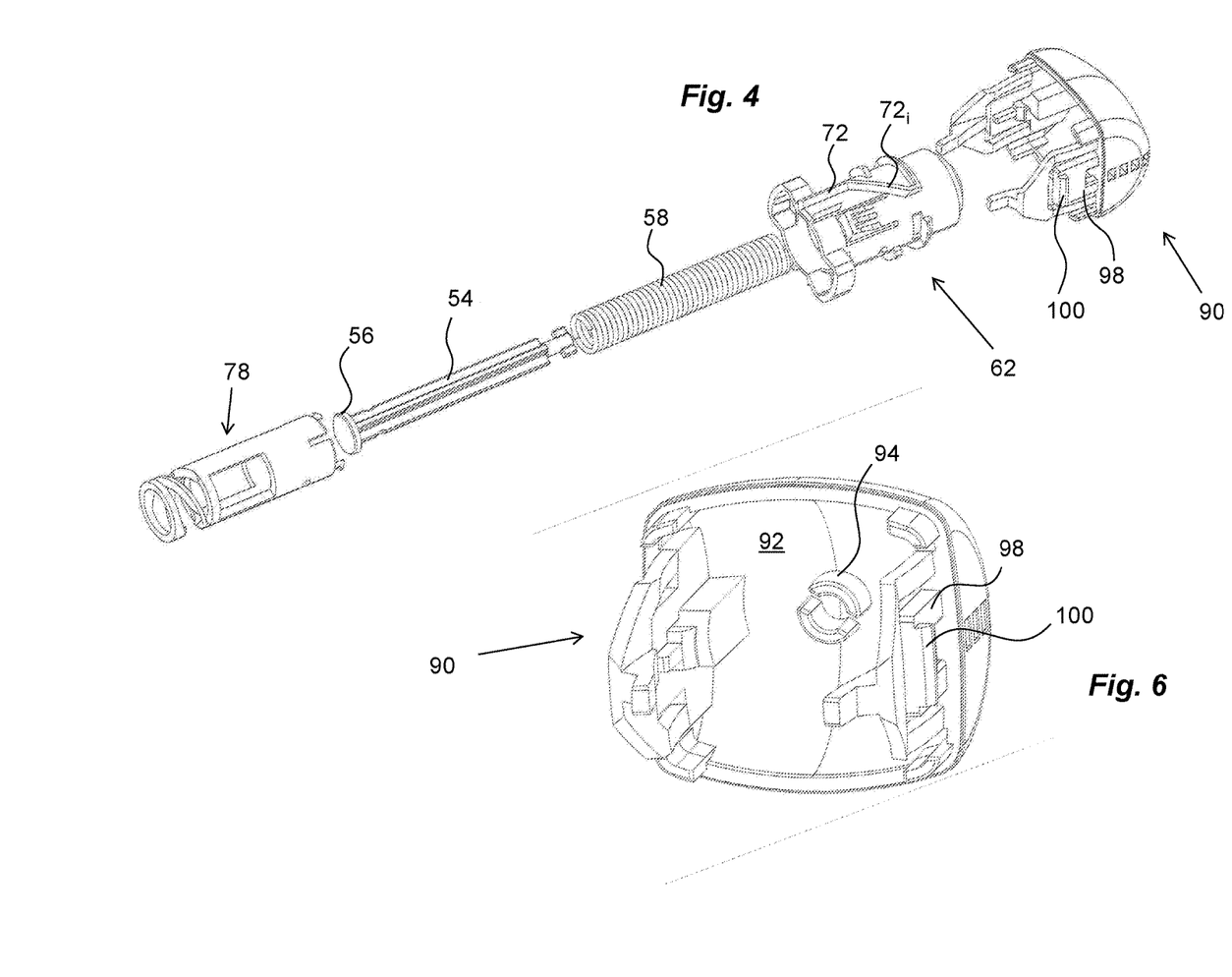

The medicament delivery device further comprises an end cap 90, FIG. 6, to be attached to the distal end of the housing. The end cap 90 has a dome-shaped end wall 92 where its proximally directed inner surface is arranged with two arc-shaped proximally extending protrusions 94 arranged such that the distal end of the plunger rod 54 with its wings 70 will engage, whereby the plunger rod 54 is rotationally locked. The arc-shaped protrusions 94 also function as guide elements together with a distally directed annular protrusion 96 on the end wall 60 of the rotator 62, providing a journal support as will be described below. The end cap 90 is further arranged with first attachment elements that in the embodiment shown comprises two proximally directed arms 98. Each arm 98 is arranged with a generally radially outwardly extending ledge 100, where the ledges 100 are to engage in second attachment elements that are in the form of recesses 102, FIG. 1, at the distal end of the housing 10 for attachment of the end cap 90 with the housing.

Figure 3A:
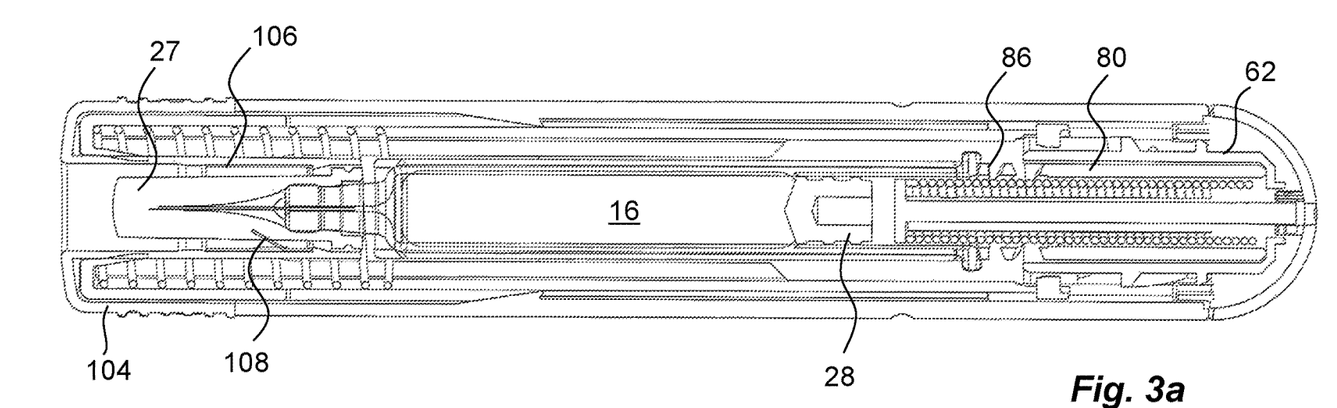
FIG. 3 is a cross-sectional view of the medicament delivery device according to FIG. 1, FIG. 4-9 are detailed views of components of the present disclosure.
Figure 3B:
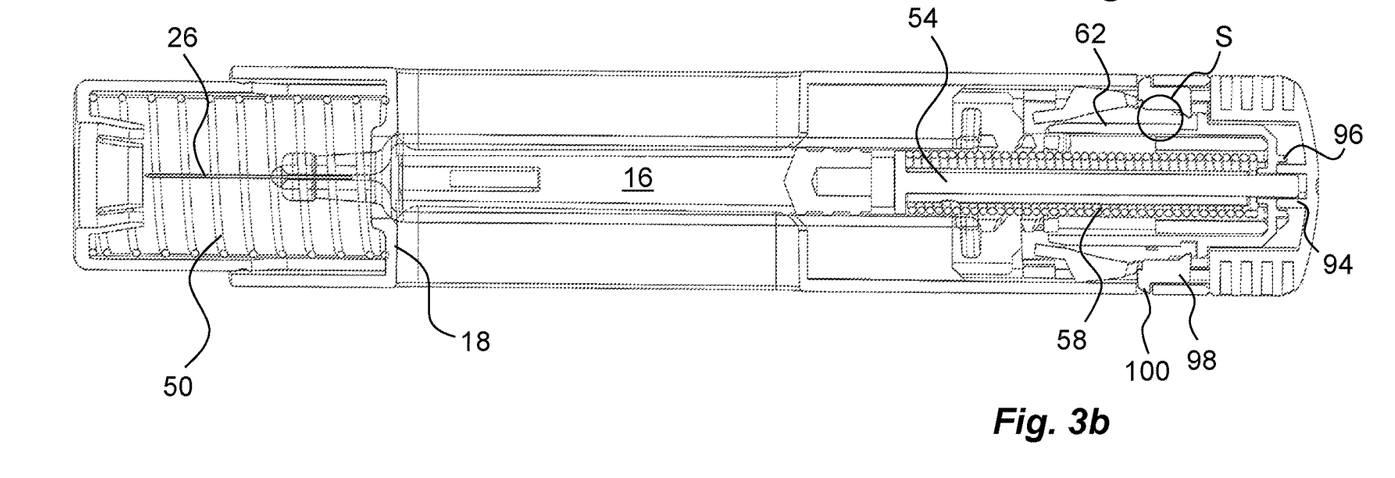

Finally, the medicament delivery device is arranged with a safety cap 104, FIGS. 1 and 3a. It comprises a generally tubular grip body designed to fit onto the proximal end of the medicament delivery device with a friction fit with the medicament delivery member guard 32. A generally tubular medicament delivery member shield remover 106 extends into the central passage of the medicament delivery member guard 32 and surrounds the medicament delivery member shield 27. The medicament delivery member shield remover 106 is arranged with proximally directed inclined tongues 108 that engage with the outer surface of the medicament delivery member shield 27 to grip it.

The device is intended to function as follows. Before delivered to a user, the end cap 90 is not yet attached and a medicament container 16 is entered into the housing 10 from the distal end 14. Thereafter the power unit 52 is placed inside the housing 10. The compression drive spring 58 is in a tensioned state with the plunger rod 54 held in place in relation to the rotator by the wings 70 engaging the land sectors 68, in a non-activated rotational position of the rotator. The end cap 90 is attached by pushing it in the proximal direction into the distal passage of the housing 10. The arms 98 of the end cap 90 will flex inwards when the outwardly directed ledges 100 come in contact with the housing 10. They can flex inwards due to the space S between the inner surface of the housing 10 and the outer surface of the rotator 62 as seen in the circle of FIG. 3b. Finally the protective cap 104 is attached to the proximal end of the medicament delivery device. The medicament delivery device may now be delivered to a user.

When a user is to administer a dose of medicament the protective cap 104 is pulled in the proximal direction. Due to the engagement of the medicament delivery member shield remover 106 with the medicament delivery member shield 27, it will be removed from the medicament delivery member 26. The next step is to press the proximal part of the medicament delivery device against a dose delivery site. This will cause the activator, i.e. medicament delivery member guard 32 to be moved in the longitudinal direction in relation to the rest of the medicament delivery device, whereby a penetration of the medicament delivery member 26 is performed. The relative movement of the medicament delivery member guard 32 will cause the protrusions 48 to slide along the guide ridges 72 of the rotator 62 such that the protrusions 48 will come in contact with the inclined sections $72_i$ of the guide ridges, FIG. 7, which will cause the rotator 62 to turn around the longitudinal axis of the medicament delivery device, FIG. 8.

Figure 8:
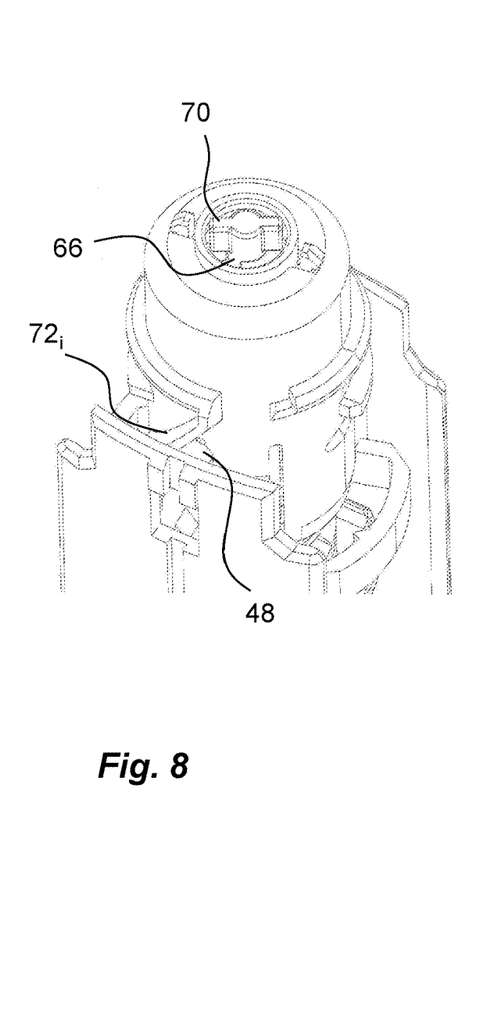

The turning of the rotator 62 will cause the cut-out sectors 66 of the passage 64 at the end wall 60 to move in relation to the wings 70 of the plunger rod 54, wherein the plunger rod 54 is prevented from turning due to the engagement with the arc-shaped protrusions 94 of the end cap 90.

Figure 9:
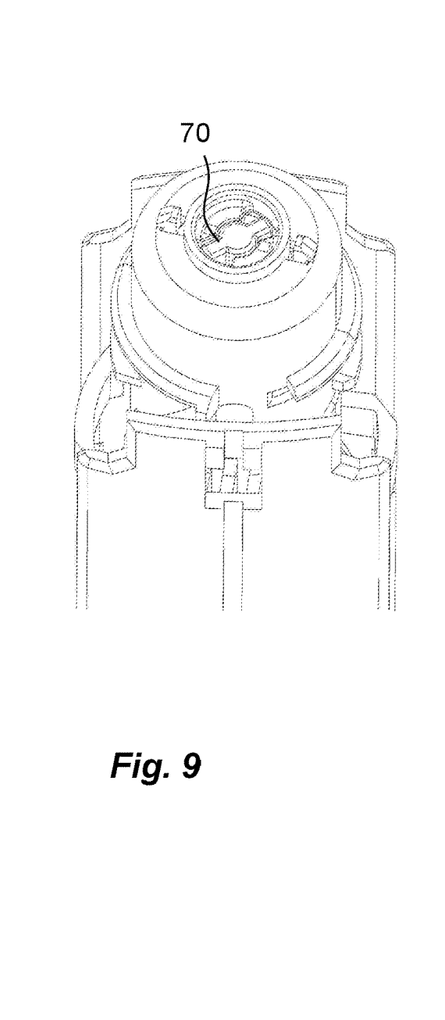
Figure 10:
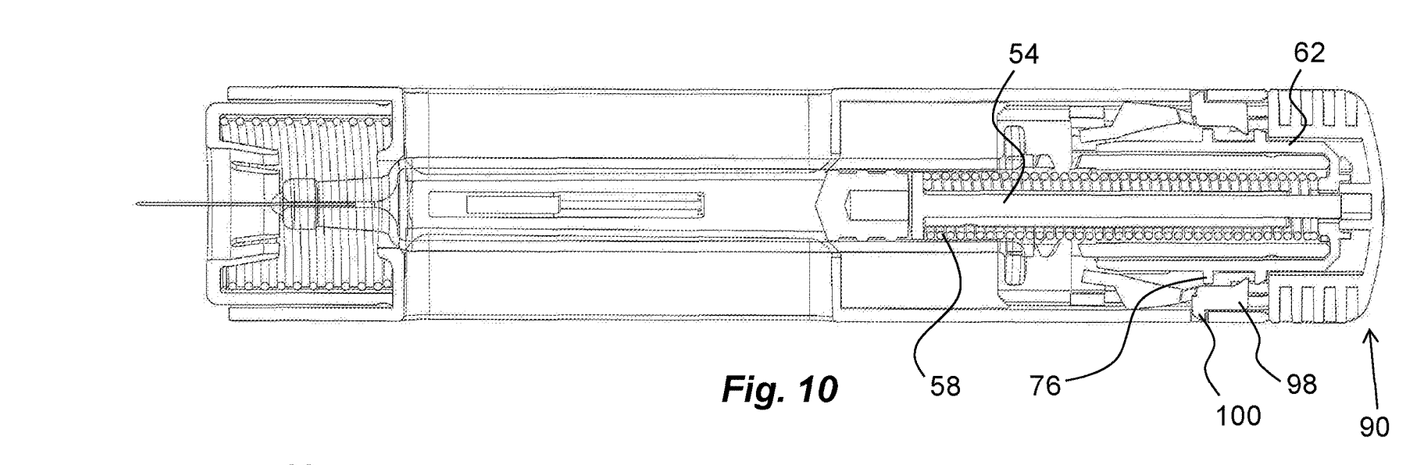
FIGS. 10-11 are cross-sectional views of different functional states of the medicament delivery device of FIG. 1.

Also, as the rotator 62 is turning, the stop ledges 76 on the outer surface of the rotator 62 are moved adjacent the free ends of the arms 98 of the end cap 90, as seen in FIG. 10. This action will prevent any movement in the radial direction of the arms 98. This aspect is important because when the rotator 62 has turned a certain rotational distance to an activated rotational position, the cut-out sectors 66 of the end wall 60 of the rotator 62 are aligned with the wings 70 of the plunger rod, FIG. 9, whereby the plunger rod 54 is released, FIG. 10. When the plunger rod is released, so is the compression drive spring 58, which will urge the plunger rod 54 in the proximal direction. However, the drive spring 58 will also exert a force on the end wall 60 of the rotator 62, and thus on the end cap 90 because of the journalled connection of the rotator 62 with the end cap 90, and this force may cause the attachment of the end cap 90 to be disengaged. However, any disengagement is prevented by the stop elements 76 on the rotator 62 effectively preventing any movement of the arms 98.

Figure 11:
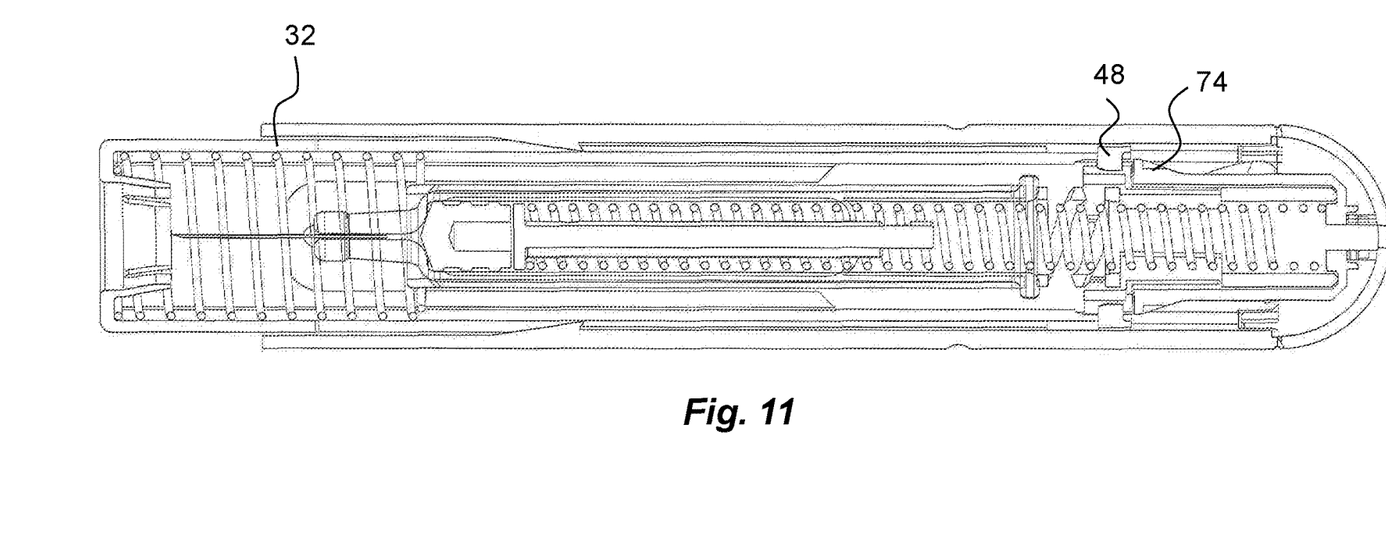

The movement of the plunger rod 54 in the proximal direction will cause it to move the stopper 28, whereby a delivery of a dose of medicament is performed through the medicament delivery member 26. When the dose has been delivered, the medicament delivery device may be removed from the dose delivery site. The medicament delivery member shield 32 will then be moved in the proximal direction by the force of the medicament delivery member shield spring 50, FIG. 11. The movement in the proximal direction of the medicament delivery member shield 32 will cause its protrusions 48 to move over the wedge-shaped protrusions 74 and be positioned proximal of the wedge 74, FIG. 11, thereby locking the medicament delivery member shield 32 in the extended position, thereby covering the medicament delivery member. The device may now be discarded.

It is to be understood that the embodiment described above and shown in the drawings is to be regarded only as a non-limiting example of the disclosure and that it may be modified in many ways within the scope of the patent claims.

The invention claimed is:

1. A medicament delivery device comprising an elongated housing extending in a longitudinal direction, which housing is arranged to accommodate a medicament container,
   an end cap arranged with a first attachment element designed to engage with a second attachment element on said housing for attaching said end cap to said housing,
   a rotator rotatably arranged inside said housing,
   an activator axially slidable with respect to the housing from an extended position to a retracted position and operably connected to said rotator such as to rotate said rotator from an initial non-activated rotational position and an activated rotational position when the activator is moved from the extended to the retracted position, a plunger rod having a distal end comprising radially extending wings that releasably engage the rotator when in the non-activated rotational position, said rotator further comprises a blocking element arranged to cooperate with said first attachment element for preventing disengagement of said first attachment element from said second attachment element when the rotator is in the activated rotational position.

2. The medicament delivery device according to claim 1, wherein said first attachment elements comprise proximally directed arms, flexible in a direction generally transverse to the longitudinal direction, outwardly directed protrusions arranged on free ends of the arms, that said second attachment elements comprise recesses arranged to accommodate said protrusions.

3. The medicament delivery device according to claim 1, wherein said rotator is generally tubular and wherein said blocking element comprises radially outwardly directed wall portions of said rotator.

4. The medicament delivery device according to claim 3, wherein said blocking element comprises radially outwardly extending protrusions arranged adjacent the free ends of said arms.

5. The medicament delivery device according to claim 4, wherein said protrusions also extend in a generally circumferential direction of said rotator.

6. The medicament delivery device according to claim 1, wherein said blocking element is arranged to prevent disengagement when the medicament delivery device is activated, but to allow attachment of said end cap with said housing and engagement of said attachment elements when said medicament delivery device is in an initial, non-activated state.

7. The medicament delivery device according to claim 5, wherein said protrusions are arranged adjacent to the free ends of said arms in rotational positions of said rotator except in said non-activated rotational position of said rotator.

8. The medicament delivery device according to claim 1, wherein said rotator is rotatably positioned adjacent the end cap.

9. The medicament delivery device according to claim 1, further comprising
a power unit comprising the plunger rod arranged to act on said medicament container for expelling a dose of medicament,
the power unit further comprising a drive spring operably connected to said plunger rod for driving said plunger rod for expelling the dose of medicament, and that said rotator comprises a plunger rod locking element for releasably locking said plunger rod with said drive spring in a tensioned state.

10. The medicament delivery device according to claim 8, wherein a plunger rod locking element is arranged to release said plunger rod when said activator has rotated said rotator to the activated rotational position.

11. A medicament delivery device comprising:
a housing extending in a longitudinal direction and having a second attachment element located on a distal end;
a medicament container;
an end cap comprising a first attachment element designed to engage the second attachment element;
a rotator rotatably arranged inside the housing and adjacent to an inside surface of the end cap;
an activator axially slidable with respect to the housing from an extended position to a retracted position and operably connected to the rotator through engagement of protrusions on a proximal end of the activator with guide ridges on an outside surface of the rotator such that axial movement of the activator in a distal direction causes rotation of the rotator from an initial non-activated rotational position to an activated rotational position;
a plunger rod having a distal end comprising radially projecting wings; and
wherein the rotator further comprises a proximal end wall having a cut-out, where the cut-out rotates from a locked position to an unlocked position as the rotator moves from the initial non-activated rotational position to the activated rotational position.

12. The medicament delivery device of claim 11 where the rotator further comprises a blocking element extending circumferentially about an outer surface of the rotator, where the blocking element engages the first attachment element preventing disengagement of the first attachment element from the second attachment element when the rotator is in the activated rotational position.

13. The medicament delivery device of claim 12 where the plunger rod is in a locked axially position relative to the rotator and housing when the wings are not aligned with the cut-out and where the plunger rod is in an unlocked position when the cut-out is aligned with the wings such that the wings can move axially through the cut-out in a proximal direction.

14. The medicament delivery device of claim 13 where the plunger rod is biased in a proximal direction by a drive spring.

15. The medicament delivery device of claim 14 where the drive spring exerts a biasing force in the distal direction on the end wall of the rotator and on the end cap.

16. The medicament delivery device of claim 15 where the engagement of the blocking element with the first attachment element prevents disengagement of the first and second attachment elements and distal movement of the end cap.

17. The medicament delivery device of claim 11 where distal movement of the activator in a proximal direction after reaching the retracted position causes the protrusions to move over wedged-shaped protrusions located on outer surface of the rotator.

18. The medicament delivery device of claim 17 where the protrusions abut a proximal facing edge of the wedge-shaped protrusions preventing axial movement of the activator in the distal direction.

* * * * *